United States Patent [19]
Perego

[11] 3,973,711
[45] Aug. 10, 1976

[54] MAGNETIC CRAWLER VEHICLE FOR SOLDERING APPARATUS

[75] Inventor: Emilio Perego, Milan, Italy

[73] Assignee: Compagnia Italiana Montaggi Industriali, Milan, Italy

[22] Filed: Mar. 6, 1974

[21] Appl. No.: 448,761

[30] Foreign Application Priority Data
Apr. 3, 1973 Italy .................................. 22539/73

[52] U.S. Cl. ................................ 228/32; 219/126; 180/1 VS
[51] Int. Cl.² ......................................... B23K 37/02
[58] Field of Search .......................... 228/32, 25, 27; 219/125 R, 125 PL, 126; 180/1 VS; 114/222

[56] References Cited
UNITED STATES PATENTS

| | | | |
|---|---|---|---|
| 2,132,661 | 10/1938 | Temple | 114/222 X |
| 3,249,733 | 5/1966 | Santilhano | 219/126 |
| 3,437,786 | 4/1969 | Colinet | 219/126 |
| 3,777,834 | 12/1973 | Hiraoka et al. | 114/222 X |

FOREIGN PATENTS OR APPLICATIONS 978,600  12/1964  United Kingdom ............... 180/1 VS Primary Examiner—Al Lawrence Smith
Assistant Examiner—K. J. Ramsey
Attorney, Agent, or Firm—Hill, Gross, Simpson, Van Santen, Steadman, Chiara & Simpson

[57] ABSTRACT

A magnetic seam tracking device designed to orientate the feed or forward motion of a soldering tool along the edges of metal sheets disposed head against head and to be submitted to the soldering operaion. The device comprises a carriage or truck B capable of retaining the soldering tool A, said carriage or truck being provided with track-chains (30), the articulated elements whereof have permanent magnets (40-42) which co-operate with metal sheets (D1) and (D2) to be soldered.

10 Claims, 9 Drawing Figures

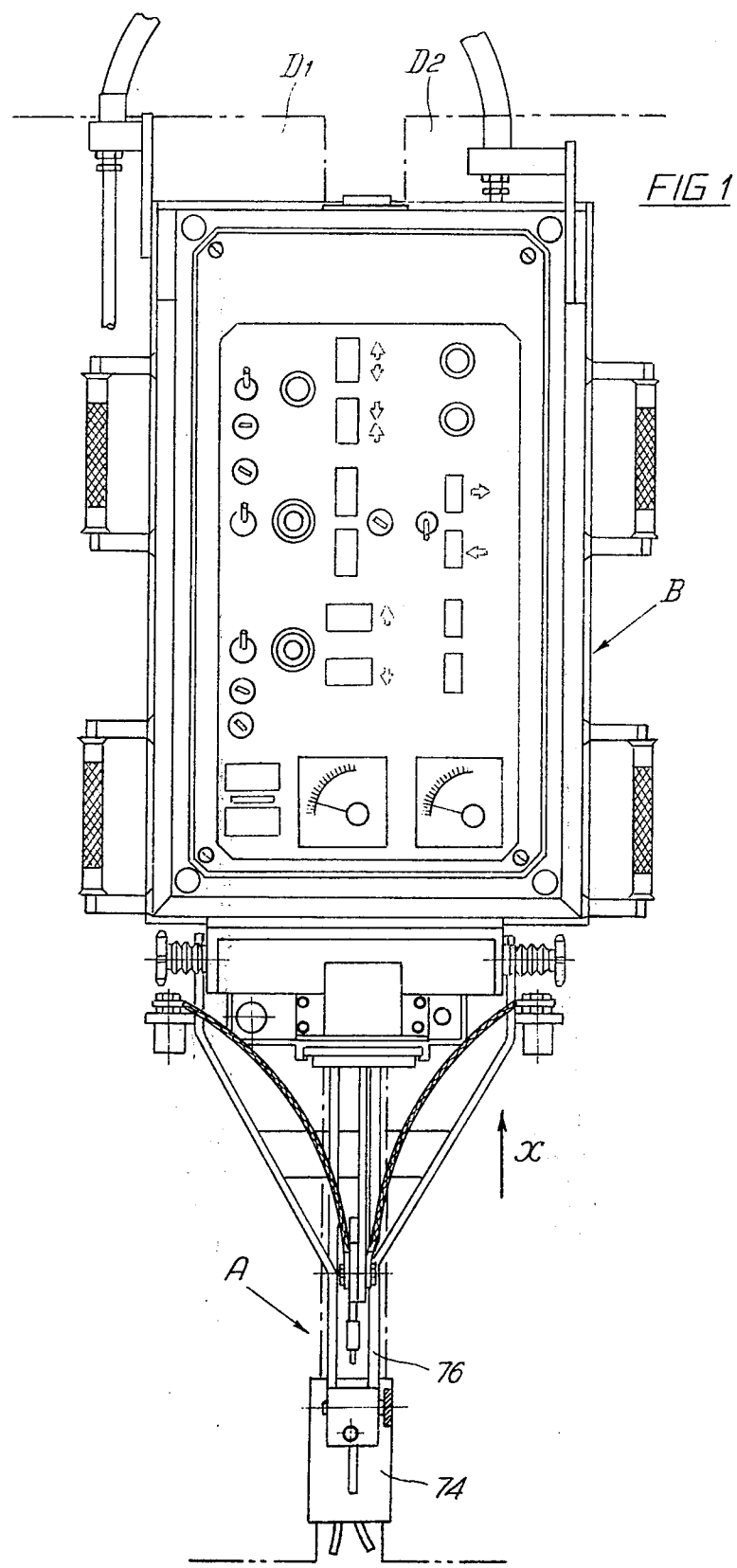

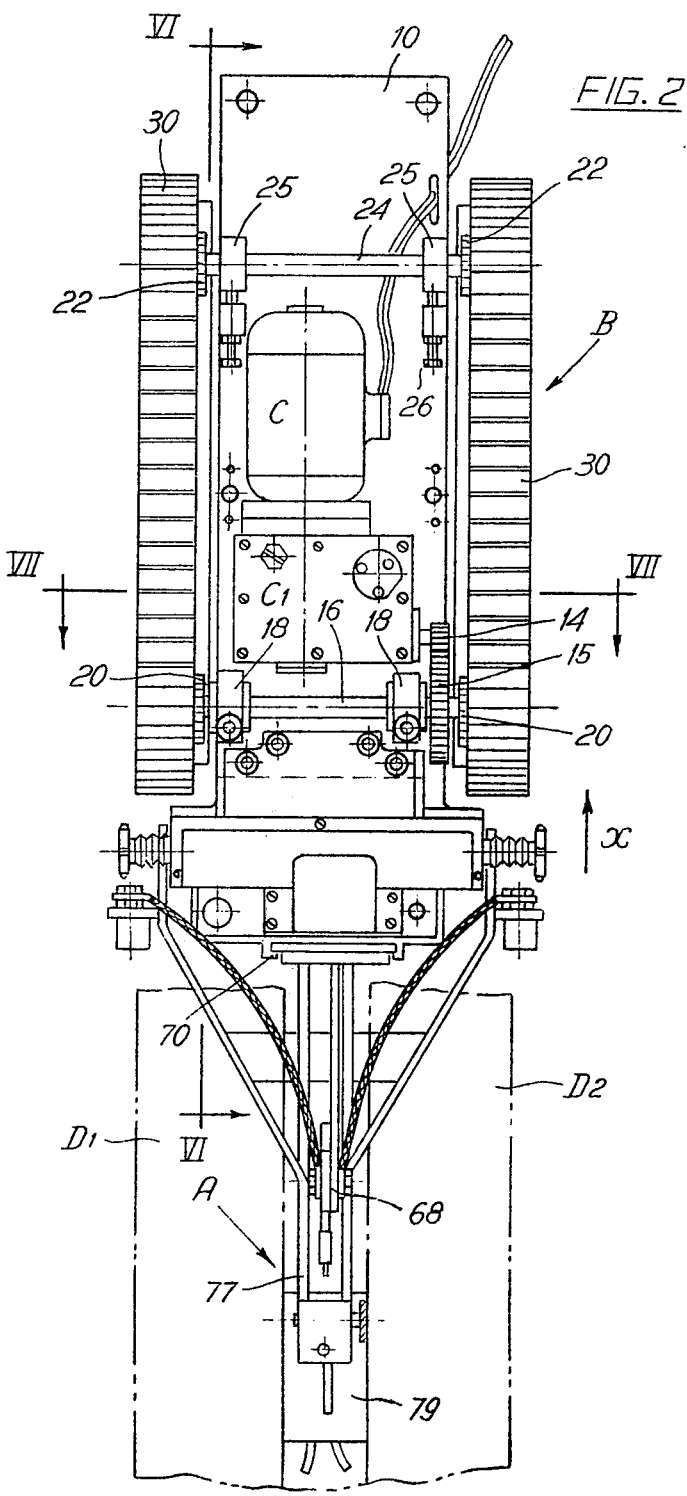

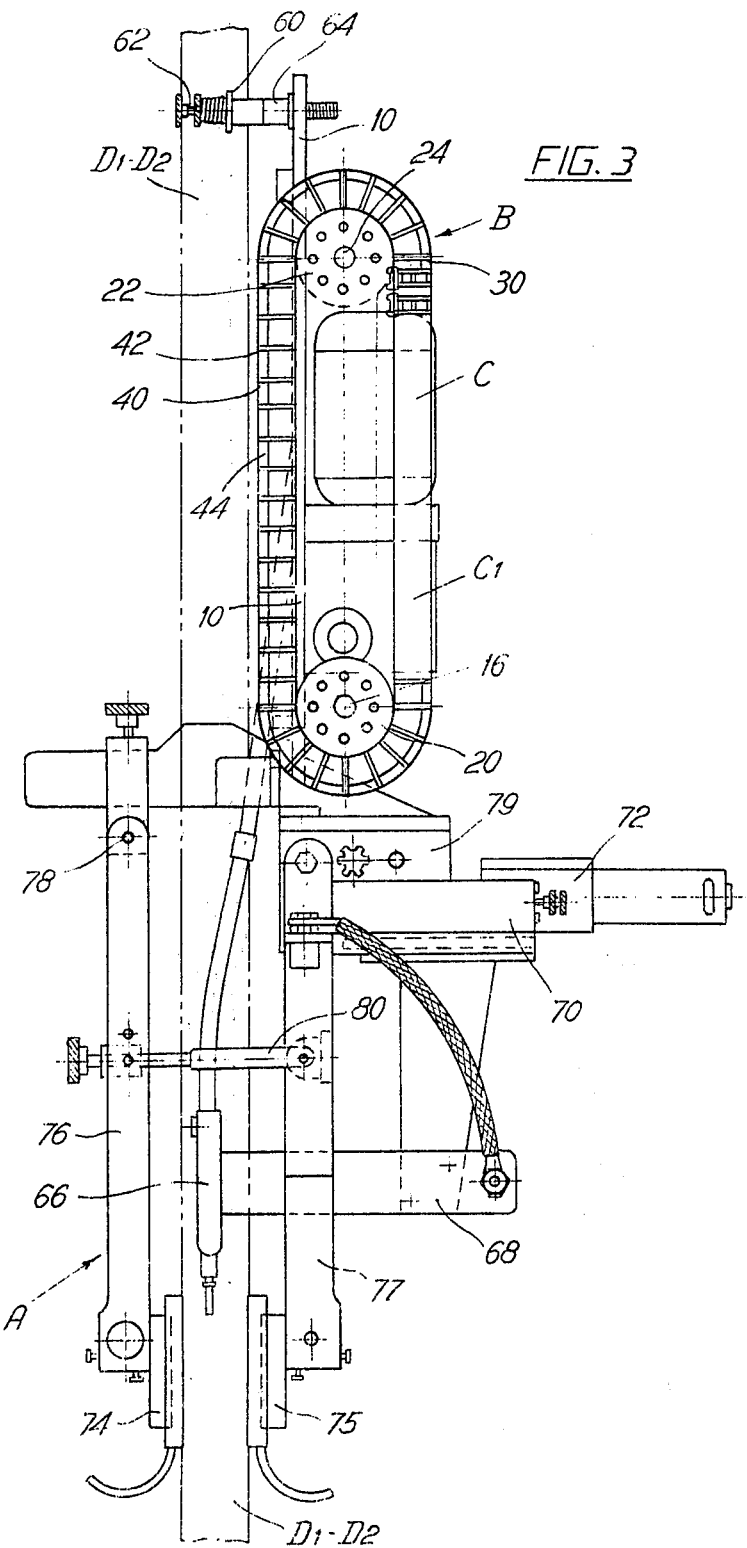

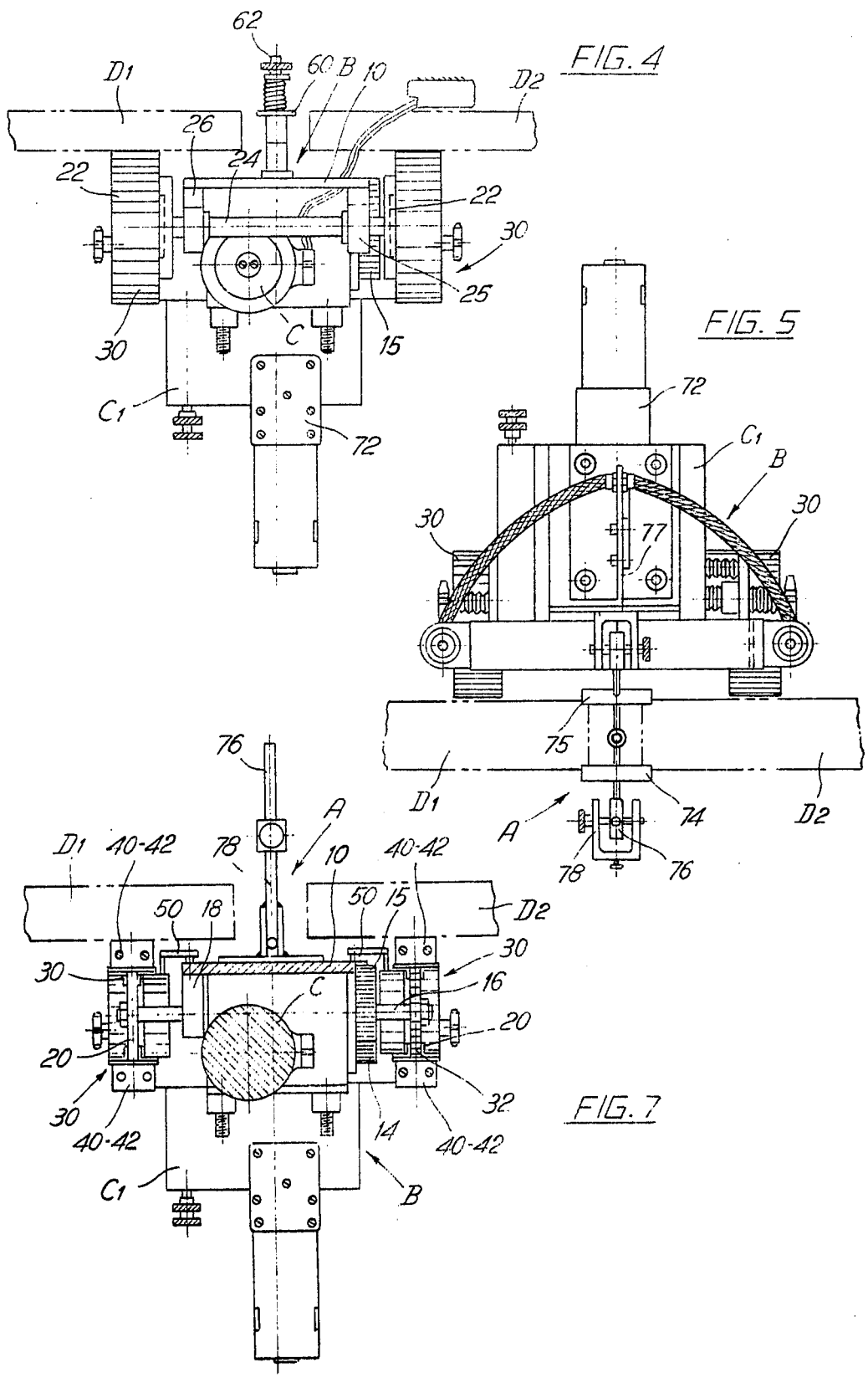

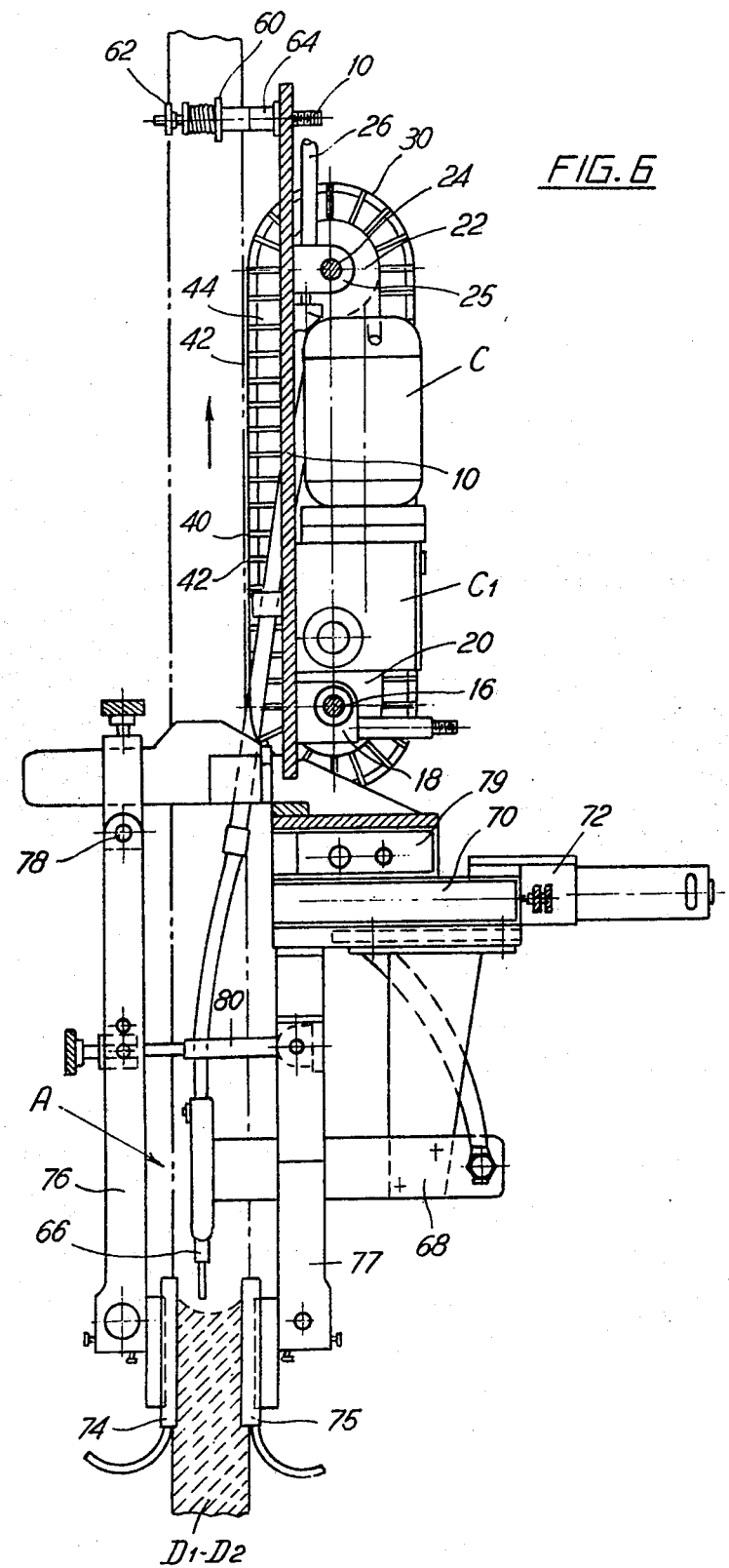

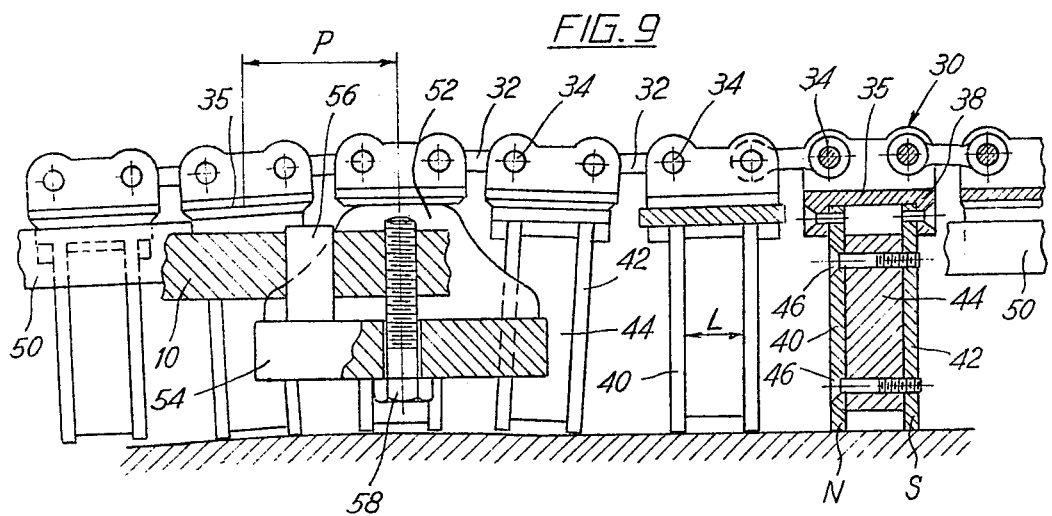
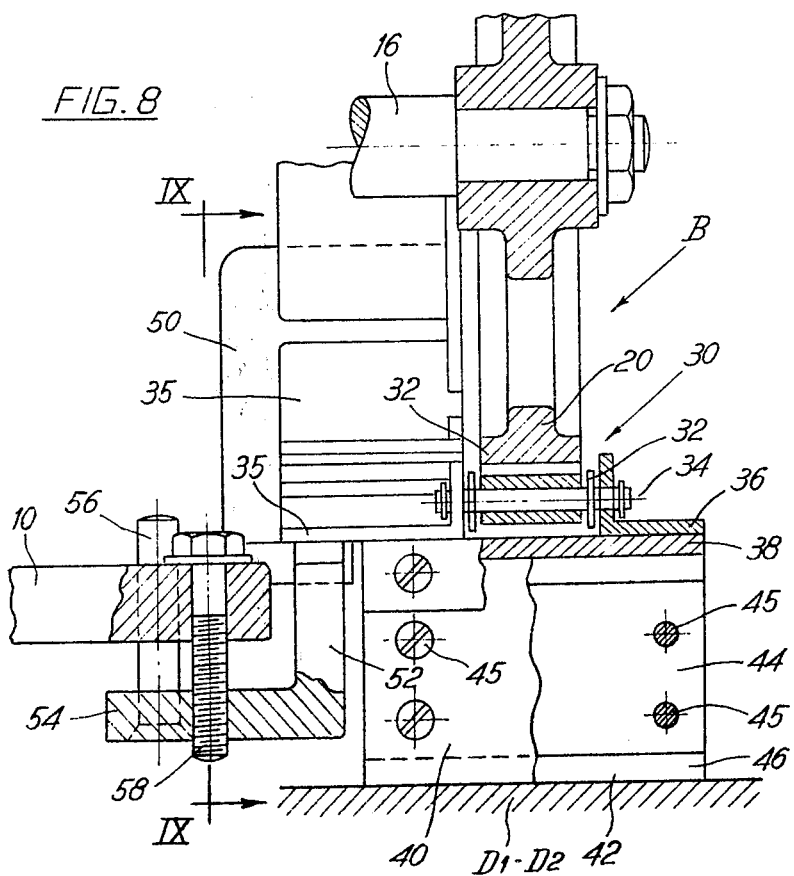

MAGNETIC CRAWLER VEHICLE FOR SOLDERING APPARATUS

The invention refers to a device to retain and displace soldering tool carrying carriages or trucks all along a soldering path for metallic materials in general and, in particular, for large size sheet metal.

With particular, although not exclusive reference to the process which is carried out to solder very large sized metal pieces, for instance such as required to prepare hulls for water craft or metallic structures in general, which it is necessary to connect to one another metal sheets, profiled pieces or other members by means of soldering effected along the limbs or edges of said pieces which are, of course, arranged in advantageous positions, according to the requirements of the dockyard and with several others, for the reason that the positions and orientation of said parts are the most different ones.

Therefore, the soldering tool is required to work, each time, in different positions, which are, in certain cases, practically impossible to realize, owing to the position and orientation of the limbs to be submitted to the soldering operation.

To carry out the solderings concerned, has been, until now, necessary to provide and to erect at the dockyard, scaffoldings capable of retaining special guides, along the areas to be soldered, such guides being of course required to travel along different and, in some cases, very irregular paths.

To solder metal sheet limbs head against head, a carriage or truck whereon an automatic unit, as well as a soldering equipment are installed, is caused to travel along said guides.

The preparation of the mountings for the guide-rails is both lengthy and expensive, in particular when the edges to be soldered are curved or if such edges extend in multilinear directions. Said situation is rendered still more critical, because the soldering apparatus known in the art do not run through satisfactory soldering paths. In other words, when negotiating said paths, no account is taken of the course of the edges to be joined, nor of the profile of the free faces or surfaces of the sheet metal or of the pieces to be soldered, inasmuch as said faces may be convex or curved.

The purpose of the present invention is, to prevent the above described and still other drawbacks, as well as to embody a device for application to soldering trucks and, at the same time, capable of ensuring a quick and easy performance of perfect soldering, independently of the nature of the edges of metal sheets or the like which have to be submitted to the soldering process, even if the faces of said metal sheets are not plane.

Another purpose of the present invention is the provision of a device of the above mentioned type, without the need to provide special guide paths for the truck all along the edges to be soldered, such device being, at the same time, capable of ensuring a regular and even feed motion of the soldering tool, which is retained in the exactly desired position between the limbs to be soldered to one another, independently of the position of said limbs with respect to one another.

Still another purpose of the present invention is to provide a device which is capable of performing perfect solderings on metal materials in general and, at the same time, of ensuring a precise orientation of the soldering tool all along the edges to be joined by means of the soldering seam.

Still another purpose of the present invention is the provision of a device which can be easily and economically fitted to soldering equipment carrying trucks, and such as to ensure a close adhesion of said trucks to the object which is subjected to the soldering operation, even if said truck encounters an obstacle or, generally speaking, a resistance during its feed or forward motion, without the danger of incurring breakages or other drawbacks.

The device claimed with the present invention, designed to retain, as well as to displace, soldering tools installed on board of such trucks as are movable along a soldering path, while the displacement of said trucks is supervised by feeling members, is characterized in that at least one flexible annular member is provided, which winds onto pulleys controlled by the feed or forward motion of the truck, such annular member retaining, through articulated means and in the desired succession, a plurality of magnetic elements, a part of which forms, with the pole shoes thereof, below the above mentioned truck, an active movable extension, said extension or length engaging magnetically a truck made of a magnetic material, which extends along at least a part of the edges of the pieces to be soldered, in such a way that said magnetic elements are forming, together with the flexible retaining and gripping member, a magnetic truck-chain to displace the truck with the desired speed, all along said edges, to be soldered to one another.

In practice, the above explained inventive idea can be realized in the form of different embodiments, without leaving however the domain of the present patent application.

For example, according to a preferred embodiment of the device claimed with the present application, the flexible annular members consist of a chain provided with articulations, to retain the magnetic elements which are winding, like truck-chains, onto twin-pulleys, in such a way that the pole shoes of said magnetic elements engage, successively, either the track or the plates of magnetic material to be soldered to one another.

The magnetic means mounted onto the magnetic elements of the magnetic chain can be comprehensive of, or can consist either of permanent magnets or of electromagnets, the pole shoes whereof are aligned in such a way as to form a predetermined length, which is the active length of the magnetic truck-chain, the extension or profile of said chain being such as to marry and match with the profile of the faces of the sheet metal to be subjected to the soldering operation. In such cases, in which the surface of said faces is curved and, generally speaking, not at a level, the active length of the magnetic chain (i.e. the length which the poleshoes of the magnetic elements co-operate with the track or with the magnetic sheet-metal to be soldered), is combined with adjustable guide members, for the purpose of allowing an advantageous course or orientation of said active length or extension, in order to ensure the adhesion of the pole-shoes of the magnetic elements pertinent to said active length or extension, to the surface of the track or of the magnetic sheet-metal to be soldered.

The invention will be now described in the following description, wherein reference is made to the annexed drawing, showing, by way of example, an advantageous embodiment of the device claimed with the present invention, fitted to a truck used to solder the edges of large sized metal sheets which, in practice, can be orientated in any desired direction as, for instance, in the case of hulls or like metal structures.

FIG. 1 is a front elevation view of a preferred embodiment of a soldering apparatus, which comprises the device according to the present invention.

FIG. 2, which is like FIG. 1, is a front elevation view of the apparatus, with the cover and the panel for the control and setting members removed therefrom.

FIG. 3 is a side elevation view of FIG. 1.

FIGS. 4 and 5 show the ends of FIG. 2, viewed from above and from below respectively.

FIGS. 6 and 7 are sections taken along lines VI—VI and VII—VII of FIG. 2.

FIG. 8 shows, on enlarged scale, a detail of FIG. 7.

FIG. 9 is a secion along line IX—IX of FIG. 8.

With reference to FIGS. 1 to 6 of the drawings, the apparatus as illustrated therein, comprises one soldering unit A, advantageously arranged on a carriage B provided with a corresponding driving motor C of an appropriate type, for instance with an electric motor, which is advantageously piloted, in order to maintain said soldering unit A in the desired position, as it moves along the edges of the metal sheets (D1 and D2) to be submitted to the soldering operation.

In the illustrated case and as it will be now described in the following, the electric motor C is of an advantageous type, said motor being fixed to a base frame 10 of carriage B and coupled to a reduction gear C1, onto the output shaft 12, whereby a pinion 14 is keyed to said shaft which is in engagement with a toothed wheel 15 keyed, in turn, to a shaft 16 retained by supports 18 to frame 10, in such a way that the axis of said shaft is orthogonal to the longitudinal axis of the above mentioned frame. Two toothed wheels 20 are keyed to the above mentioned shaft 16, each of said wheels being combined with a corresponding transmission wheel 22. Like the two wheels 20, said two wheels 22 are keyed to the ends of a shaft 24 supported by frame 10 through tensioning members 26, to allow adjustment of the center distance between shafts 16 and 24, for the purpose as set forth in the following.

A flexible, endless member 30 winds onto each of the coplanar wheel-pairs 20, 22, arranged sideways to the longitudinal axis of carriage B.

In each of the illustrated case, the above mentioned members 30 comprises at least one chain 32, for example a Galle-chain. A plurality of pivots 34 of said chain retain twin square-pieces 35-36 (see FIGS. 8 and 9) disposed, with the respective elements thereof, at the lateral ends of the above mentioned chain, in such a way that the free wings of the elements forming each one of said twin square-pieces are coplanar and opposed.

The free wings of each of twin square-pieces 35-36 provide brackets, sideways to chain 32 and each of said pieces 35-36 is connected to and retains a small-sized plate 38 made of magnetic material.

Spaced twin plates 40-42 are fixed to the free face of and project from each one of said plates 38 and a block 44 is inserted between the elements of said twin-plates, said block being tightly secured by means of screws 46.

The periphery of blocks 44 is less than that of twin plates 40-42 forming below the blocks a hollow space or gap 46, defined by the free distal edges of the two above mentioned plates 40-42 which can mate with the faces of the metal sheets D1 and D2.

Each of said three pieces 40-42-44 forms an individual magnetic element, in which block 44 is a permanent magnet with a considerable gripping capacity; for instance, such magnet is made of a sintered material or otherwise of an Al-Ni-Co-alloy. On the other hand, twin-plates 40-42 are made of a magnetic, preferably of a highly permeable magnetic material, the free distal edges whereof are forming coplanar pole shoes N-S, arranged at the outer periphery of each one of the flexible magnetic members 30, designed to support the above mentioned magnetic elements.

The units formed with the magnetic elements 40-42-44 are connected to chain 33, in such a way that the pole shoes N-S thereof form, together with those of the adjacent units, a succession of pole shoes N-S, pertaining to the permanent magnets 44. The magnetic circuits of each of the magnetic elements are provided within the active extension or length of magnetic chain 30, and said circuits are closed at the lower part thereof, when the pole shoes N-S of such circuits are in engagement with the surface of the magnetic track which, in the present case, consists of plates D1 and D2 of a magnetic material, to be soldered to one another. The various magnetic groups or elements (each of which consisting of a permanent magnet 44 and of plates 40-42) form, as above mentioned, an uninterrupted successsion of pole shoes N-S, having a substantially constant pitch which is selected in accordance with the features of the apparatus onto which the device is applied.

As mentioned, in order to meet the requirements of the end-users of the illustrated device, said device has been so conceived as to be capable of soldering the plane and/or the curved edges of said plates D1 and D2.

In both of the aforementioned cases, it is necessary to ensure a close and perfect adhesion of the active length or extension of magnetic chains 30 of equipment B, to the metal sheets D1 and D2, in accordance with the course of the surface of said sheets, with particular regard to the pole shoes of the whole number of magnetic elements 40-42-44, which must adhere to the surfaces of said sheets D1 and D2 in such a way as to prevent any discontinuities between said sheets and the pole shoes of said magnetic elements, discontinuities which would be prejudicial to a perfect adhesion of apparatus B to said metal sheets D1 and D2.

According to the present invention, the device provides such members as are capable of ensuring, at all times, the adhesion of pole shoes N-S of the composite magnets 40-42-44 of the lower length or outer length of magnetic chains 30, to the surfaces of plates D1 and D2, independently of the course of said surfaces which, as mentioned, may ba plane and/or curved.

For this purpose, each of magnetic chains 30 (formed with the flexible member 32 and with the composite magnets 40-42-44), is provided with guide and orientation members, in order to ensure the due course of said chains and, in particular, that of the outer or lower extension thereof, in such a way that the whole number of pole shoes N-S adhere to the surfaces of plate D concerned.

With reference to FIGS. 8 and 9, the guide and orientation members for magnetic chain 30 consist of tracks or guide-rails 50 integral with frame 10 of the apparatus, said tracks following the desired course and being so disposed as to engage the lower or outer extension of said magnetic chain; furthermore, such tracks extend between the elements of each of the pairs of toothed wheels 20-22.

The guide-rails 50 are disposed inside the wings provided by square-pieces 35. It should be noted that, in accordance with the end-user's requirements, the middle straight length of the guide-rails is that designed to ensure the coplanarity, as well as the adhesion of the whole number of pole shoes N-S formed with plate-pairs 40-42, to the surface of plates D1-D2 to be subjected to the soldering operation, in such a way as to maintain said adhesion unaltered, independently from the profile of the above mentioned plates D1-D2, from the forward or feed motion of the outfit or apparatus and from the stresses to which chain 30 may be however subjected, due to the possible obstacles the apparatus could encounter on its way. In such cases, wherein plates D1-D2 to be soldered have curved surfaces, the adhesion of magnetic chain 30 is realized, by equipping the apparatus of the invention with adjustable members, designed to modify, as well as to control, the course of the outer straight length of said magnetic chain, comprised between the pairs of toothed wheels 20-22 and to ensure, in regular succession, the disengagement from and the engagement in pole shoes N-S, of the surfaces of plates D1-D2.

As shown in FIGS. 8 and 9, an adjustable member designed to modify the course of the straight length of magnetic chain 30 is combined with guide-rails 50. In other words, the guide-rails concerned are interrupted at the middle part thereof, comprised between the elements of twin-pulleys 20-22. The above mentioned setting or adjusting member is disposed within each one of the cavities formed by said interruptions. Said setting or adjusting member consists of one or more sliders 52, which are advantageously shaped; and each of said sliders is so arranged, as to allow the co-operation of the free end thereof with the lower face of square-pieces 35 of chain 32. Each of sliders 52 is fixed to a plate 54 having at least one guide pin 56, which fits slidably into a corresponding opening, said opening being either directly provided by base-frame 10, or by a complemental member fixed to said base-frame 10. As a consequence, by acting on adjusting set-screws 58, slider or sliders 52 are displaced, in such a way that the profiled surface of said sliders come, more or less, in engagement with the path for the projecting parts of square-pieces 35, in order to modify and to vary, as required, the course of the straight length of magnetic chain 30, so as to direct the pole shoes N-S of twin plates 40-42 as desired.

Special mention is made of the fact, that the presence of said advantageously adjusted sliders 52 ensures, at any time, the engagement with and the adhesion of the faces of pole shoes N-S to the faces of metal sheets D, even if said faces are not plane, inasmuch as they guide the articulated elements of magnetic chain 30 to displace and to settle as desired, independently from possible unevenness of the metal sheets and from such plays as may occur between the elements of the magnetic chain or between other parts of the apparatus.

The magnetic circuits for the magnetic chains of the device claimed with the present invention meet with the requirements of the apparatus concerned and with the scopes said apparatus is designed to realize. Furthermore, it is possible to ensure, at any time, both the adhesion of the apparatus to plates D1-D2 to be subjected to soldering, as well as the regular and uniform displacement of said apparatus exactly along the path, wherein the soldering process is to be executed. The soldering concerned is carried out by using any one of the units A of a well known type, insofar as the weight and the overall dimensions of said units do not interfere with the normal use of the device according to the present invention, because, if the weight of said outfit is considerable, the structure of the apparatus must be correspondingly sized, in particular by providing a greater active length of the magnetic chains 30 between pulleys 20-22.

The above described apparatus permits easily attaining suchh operating and safety conditions as are needed in practice, whereas said conditions cannot be always obtained with prior apparatus. In particular, when the apparatus known in the art meet obstacles during their feed or forward motion, drawbacks and breakdowns occur, causing considerable damage, in particular if the solderings are carried out along upright metal sheets since, in such cases, the apparatus is subject to falling. On the other hand, in the case of the present invention, when the apparatus performs vertical solderings; or otherwise, if same is applied below metal sheets D1, D2 and furthermore, if the apparatus concerned meets resistances or obstacles during its feed or forward motion, said motion comes to a stand still, without breakages or overloads of the elements forming the kinematic chain, which connects motor C with pole shoes N-S of the magnetic elements. When apparatus B comes to a standstill, magnetic chain 30 continues moving, whereby pole-shows N-S of the magnetic elements pertaining to the active length perform a sliding motion along the faces of metal sheets D1, D2, thus preventing the danger of breakage and, first of all, the detachment of the apparatus from said metal sheets, which, otherwise, would drop down.

Further advantages are provided by the apparatus of the present invention, in particular an even feed or forward motion. In other words, the engagement of pole shoes N-S of magnetic elements 40, 42, 44 with plates D1-D2 as well as the disengagement of said pole shoes from said plates, proceed regularly and evenly, i.e. without excessive stresses nor efforts which could impair the arrangement as well as the feed motion of the apparatus all along the edges to be soldered to one another.

As a matter of fact, the engagement of pole shoes N-S with plate-surfaces D1, D2, as well as the disengagement of said pole shoes from said surfaces, proceed evenly and by degrees, owing to the special arrangement of the permanent magnet axes along magnetic chain 30. In particular, at the ends of the active length of said chain, the axes of permanent magnets 44 are always disposed according to a normal or perpendicular surface to the engaging surfaces, which consist of the faces shown by plates D1, D2, independently from the form of said surfaces, which can be either plane or curved; in this latter case, said axes are normal or perpendicular to the tangent to the curved surface. The exact position of the magnetic elements 40, 42, 44, as shown by the magnetic chain 30, are ensured and realized, not only by setting sliders 52, but also appropriately by means of stretching members 26 in order to ensure the due tension of chain 32 and the adhesion of pole shoes N-S to the surface of metal sheets D1, D2 but, at the same time, permitting a certain flexibility of magnetic chain 30, in order to ensure the necessary adjustment of the above mentioned faces during the feed motion of the chain, that is, without influencing, nor stressing, the pole shoes of the magnetic elements which are next adjacent to the magnetic element concerned, which is either in its final or in its initial or starting position, as referred to the active length of said magnetic chain 30.

It is to be understood that modifications and/or variations can be brought to the above described and illustrated device, according to the features of the apparatus claimed with the present patent application, in particular according to the characteristics distinguishing carriage B, to which the device is fitted.

With particular reference to magnetic track or chain 30, said chain can be provided with different details, in order to achieve the desired results. For instance, pole shoes N-S formed with plates 40-42 can be made of a highly permeable magnetic material and, in particular, said pole shoes can be made of sintered materials, so as to obtain, in each single case, the desired shapes and profiles; likewise, permanent magnets 44 can be realized with materials having a high gripping force and in such a way as to show the desired shapes.

It is obvious that the permanent magnets 44, the magnetic chain 30 is made of, can be realized as well with electromagnets, the coils thereof ending with contacts co-operating with brushes fixed to frame 10 of the apparatus concerned, in such a way as to feed but such electromagnets as are inserted, in accordance with the single requirements, into the active length of magnetic chain 30, i.e. according to the desired feeding or forward motion of carriage B.

In order to insure magnetic adhesion of the magnetic crawler vehicle to the metal sheets D1-D2 with maximum efficiency, the pivots 34 by which the magnet units 40-42-44 are coupled through the links 32 are desirably located substantially in the planes of the respective pole shoe plates 40 and 42. In addition, the pitch P (FIG. 9) of the magnetic shoe units (considering the plates 40 and 42 which provide the pole shoe traction surfaces and the magnet blocks 44 as a unit in each instance) is selected by taking into account the width L of the magnet blocks 44, and more particularly the spacing between the plates 40 and 42 maintained by the intervening magnet blocks 44. This provides properly proportioned free space between each of the magnetic shoe units.

It is to be understood that the field of protection claimed with the present patent application extends, as well, to the automatic control of apparatus provided with the device according to the present invention. Such apparatus may be equipped with one or more than one soldering tools of any of the types known in the art, as well as with feelers of the mechanical and/or electric and/or the pressurized fluid type, in order to be able to pilot the soldering tool exactly all along the soldering path.

According to the present invention, the above described apparatus allows for the application and use of mechanical feelers. In one arrangement, as shown in FIGS. 3, 4 and 7, said feelers comprise of one or several disks 60 retained by means of a rod 62, linked to a tube 64, fixed to frame 10 of carriage B. The edge of disk 60, which co-operates with the walls of opposed limbs of metal sheets D1-D2, causes rod 62 to perform a swinging motion with respect to its own axis, which is normal or perpendicular to the faces of plates D1-D2.

The free end of rod 62 serves to actuate electric or pneumatic members inserted in the circuit, said members controlling the fed of appropriate motors designed to displace, either directly or through servomotors, carriage B in such a way as to orientate the longitudinal axis of said carriage advantageously with respect to the axis of symmetry which is formed with the opposed edges of the two plates D1-D2 to be submitted to the soldering operation.

In the illustrated case, feeler 60-62 is situated in advance of soldering unit A and hence in such a way as to maintain soldering nozzle 66 exactly between the opposed edges of the two metal sheets D1 and D2. The soldering nozzle is retained in the working position shown in FIGS. 2 and 6 by means of an arm 68 restrained to frame 10 of the apparatus by means of adjusting members 70-72, such members allowing for the orientation of nozzle 66 in the desired direction, said nozzle being retained between the edges of the above mentioned metal sheets D1-D2.

Soldering nozzle 66 is combined with containment plates 74-75 which are maintained in engagement with the faces of plates D1-D2 in such a way as to close, at said nozzle 66, the opening formed with the edges of said plates and to retain there the molten metal of the soldering seam during the cooling stage thereof. The plates 74-75 are attached to corresponding arms 76-77 by means of members allowing for the adjustment of said arms in such a way as to adapt containment plates 74-75 to the thickness of the metal sheets, as well as to the size of the slit formed with metal sheets D1 and D2 which are disposed edge-to-edge.

Arms 76-77 are maintained close to each other by means of a spring biasing element 80, in such a way that containment plates 74-75 are firmly retained against the metal sheets to be submitted to the soldering operation. In case that metal sheets D1 and D2 are not made of a magnetic material, the apparatus is maintained in the soldering position by making use of tracks or guides of a magnetic material and advantageously fixes all along the edges to be soldered to one another.

Owing to the new and improved features of the device claimed according to the present invention, it is not necessary that the magnetic tracks along which the apparatus supporting said device moves forward, be continuous and extend along all of the edges to be soldered to one another, inasmuch as it is possible to provide, i.e. to realize said tracks with advantageous interruptions or discontinuities, for instance along the deviations or curves formed between the different soldering seams, because the interruption areas are overcome owing to the characteristics of the structure of the magnetic tracks or chains 30, provided that the width of the above mentioned interruptions be not greater than certain values of pitch P of the magnetic chain elements.

I claim:

1. A magnetic crawler vehicle especially adapted for running soldering apparatus along a joint between metal members to be solder-joined, the vehicle being provided with member-engaging endless crawler track means, and means for driving the track means, said track means comprising:

magnetic shoe units which have respective pairs of spaced generally coextensive magnetic pole plates; said shoe units being articulated in spaced relation in an endless chain disposed inwardly relative to said units and including links;

respective permanent magnets fixed between the pole plates;

said plates having traction shoe surfaces projecting beyond the respective magnets and operable in magnetic traction along said joint;

and means pivotally connecting said links to the shoe units generally in the planes of said plates.

2. A magnetic crawler vehicle according to claim 1, wherein said shoe surfaces comprise edge portions of said plates of substantial length projecting in parallel relation beyond the respective magnets.

3. A magnetic crawler vehicle according to claim 1, including attachment plates secured to proximal portions of said pole plates, and said connecting means connecting said links to said attachment plates.

4. A magnetic crawler vehicle according to claim 3, wherein distal portions of said magnetic unit plates project substantially beyond the respective magnets.

5. A vehicle according to claim 3, including laterally extending guide surfaces structure on said attachment plates.

6. A magnetic crawler vehicle according to claim 1, wherein said plates have proximal portions which project beyond the respective magnets and distal portions projecting beyond the magnets and providing said traction surfaces, and means securing the plates to the magnets.

7. A magnetic crawler vehicle according to claim 1, including a frame providing support for the endless track means, guide structure on the track means, and adjustable guide means on the frame coacting with the guide structure on the track means for controlling orientation of the track means with respect to the profile of surface along which the track means travels.

8. A magnetic crawler vehicle especially adapted for running soldering apparatus along a joint between metal members to be solder-joined, the vehicle being provided with member-engaging endless crawler track means, and means for driving the track means, said track means comprising:

articulated magnetic shoe units which have respective pairs of spaced generally coextensive magnetic pole plates;

respective permanent magnets fixed between the pole plates;

said plates having traction shoe surfaces projecting beyond the respective magnets and operable in magnetic traction along said joint;

a frame providing support for the endless track means;

guide structure on the track means;

and adjustable guide means on the frame coacting with the guide structure on the track means for controlling orientation of the track means with respect to the profile of surface along which the track means travel.

9. A magnetic crawler vehicle according to claim 8, wherein the guide structure on the track means comprises guide surfaces extending laterally relative to the magnetic shoe units, and said adjustable guide means carried by the frame comprises a slider engageable with the guide surfaces.

10. A magnetic crawler vehicle according to claim 9, wherein said guide means carried by the frame comprises a member adjustably secured to the frame by adjustment screw means.

* * * * *